(12) United States Patent
Wang et al.

(10) Patent No.: US 9,610,174 B2
(45) Date of Patent: Apr. 4, 2017

(54) INTERVERTEBRAL IMPLANT

(71) Applicant: METAL INDUSTRIES RESEARCH&DEVELOPMENT CENTRE, Kaohsiung (TW)

(72) Inventors: Wei-Ching Wang, Kaohsiung (TW); Yen-Nien Chen, Kaohsiung (TW); Tzyy-Ker Sue, Kaohsiung (TW); For-Son Wang, Taichung (TW); Wei-Jen Shih, Kaohsiung (TW); Wei-Te Chen, Changhua County (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 0 days.

(21) Appl. No.: 14/335,251

(22) Filed: Jul. 18, 2014

(65) Prior Publication Data

US 2015/0150689 A1    Jun. 4, 2015

(30) Foreign Application Priority Data

Nov. 29, 2013   (TW) .............................. 102143685 A (51) Int. Cl.
| | | |
|---|---|---|
| *A61F 2/44* | (2006.01) | |
| *B22F 3/11* | (2006.01) | |
| *B22F 7/06* | (2006.01) | |
| *C22C 1/04* | (2006.01) | |
| *A61L 27/04* | (2006.01) | |
| *A61L 27/56* | (2006.01) | |
| *B22F 3/10* | (2006.01) | |
| *B22F 5/00* | (2006.01) | |
| *A61F 2/30* | (2006.01) | |

(52) U.S. Cl.
CPC .............. *A61F 2/447* (2013.01); *A61L 27/04* (2013.01); *A61L 27/56* (2013.01); *B22F 3/1109* (2013.01); *B22F 3/1121* (2013.01); *B22F 7/06* (2013.01); *C22C 1/0458* (2013.01); *A61F 2002/30011* (2013.01); *A61F 2002/30957* (2013.01); *A61F 2002/30968* (2013.01); *A61F 2002/4475* (2013.01); *A61F 2310/00011* (2013.01); *A61F 2310/00023* (2013.01); *A61L 2430/38* (2013.01); *B22F 3/10* (2013.01); *B22F 5/00* (2013.01)

(58) Field of Classification Search
CPC ......................................... A61F 2/4455–2/447
See application file for complete search history.

(56) References Cited

U.S. PATENT DOCUMENTS

| 8,361,150 B2 | 1/2013 | Zhang et al. | |
| 2001/0047207 A1* | 11/2001 | Michelson | .............. A61F 2/446 |
| | | | 623/17.11 |

(Continued)

FOREIGN PATENT DOCUMENTS

| CN | 101279106 | 10/2008 |
| CN | 202086620 | 12/2011 |

*Primary Examiner* — Nicholas Plionis
(74) *Attorney, Agent, or Firm* — WPAT, PC; Justin King (57) ABSTRACT

An intervertebral implant is a porous structure formed of a plurality of metal balls, and the intervertebral implant includes a bone support area and a bone growth area. The bone support area and the bone growth area each have a plurality of connecting holes, and a porosity of the bone support area is smaller than that of the bone growth area.

7 Claims, 8 Drawing Sheets

(56) References Cited

U.S. PATENT DOCUMENTS

| | | | |
|---|---|---|---|
| 2003/0050700 A1* | 3/2003 | Kihara | A61B 17/7071 623/17.11 |
| 2005/0177237 A1* | 8/2005 | Shappley | A61F 2/28 623/17.11 |
| 2008/0172131 A1* | 7/2008 | Trieu | A61B 17/7095 623/23.73 |
| 2010/0234966 A1* | 9/2010 | Lo | A61F 2/4455 623/23.51 |
| 2011/0071635 A1* | 3/2011 | Zhang | B32B 15/08 623/17.11 |
| 2011/0313538 A1* | 12/2011 | Oh | A61L 27/56 623/23.61 |
| 2013/0274886 A1* | 10/2013 | Matsumoto | A61F 2/442 623/17.16 |
| 2014/0094919 A1* | 4/2014 | Mantri | A61F 2/442 623/17.16 |
| 2015/0112438 A1* | 4/2015 | McLean | A61F 2/447 623/17.16 |

* cited by examiner

INTERVERTEBRAL IMPLANT

CROSS-REFERENCE TO RELATED APPLICATION

This application claims the benefit of Taiwan Patent Application No. 102143685, filed on Nov. 29, 2013, which is hereby incorporated by reference for all purposes as if fully set forth herein.

BACKGROUND OF THE INVENTION

Field of Invention

The present invention relates to an intervertebral implant, and more particularly to an intervertebral implant formed of a plurality of metal balls having a uniform particle diameter; the intervertebral implant has a number of areas, where each area is formed with a different porosity and pore size based on a different forming quantity of metal balls, making the intervertebral implant a composite pore structure having multiple stiffness.

Related Art

Lumbar interbody fusion is to remove an intervertebral disc from two cervical vertebrae and then to fuse the two cervical vertebrae. Such a step is also referred to as "spinal fusion", and is usually used for treating patients suffering from continuous back pain, sciatica or fatigue and weakness of two legs caused by spinal diseases such as spondylosis and intervertebral disc herniation.

An existing intervertebral fusion implant has problems such as an undesirable fusion effect and dislocation after bone implantation. Therefore, auxiliary treatment methods such as artificial bones, growth factors, and drugs are often utilized clinically to improve a degree of fusion of a cervical vertebra bone and an implant. However, in the case of utilizing additional adding manners, the manners have problems such as a short release period and uneven concentration in local areas. Therefore, a porous structure is arranged on an implant to enable bone growth in pores to improve a degree of fusion of the implant in a bone.

In the prior art, for example, a human cervical interbody fusion device using bioactive porous titanium alloy is disclosed in China Patent No. 202086620. The human cervical interbody fusion device using bioactive porous titanium alloy has regular pores at the circumferential portion, the average pore diameter being 300 μm to 400 μm, and the porosity being 40% to 50%; but has bony trabeculae-form irregular pores at the central portion, the average pore diameter being 400 μm to 1000 μm, and the porosity being 60% to 80%. rhBMP-2 or gelatin microspheres are attached in pores between the circumferential portion and the central portion. The porous structure and a bioactive factor sustained release system inside the porous structure can induce growth of new bone tissues, which solves the problem of fusion of a bone and a material interface, and achieves higher mechanical compatibility and bone integration capability than those of a dense material. However, for the central portion that has bony trabeculae-form irregular pores, such a structure is difficult to form. Currently metal-powder laser-sintering forming equipment still cannot achieve joint between an irregular inner portion and a regular outer portion, and pore sizes are uneven, resulting in that different stresses are easily generated in the structure.

In the prior art, for example, a gel injection molding fabrication method of a porous titanium-cobalt alloy medical implant is disclosed in China Patent No. CN101279106, which relates to the technical field of medical material fabrication. Prepare a pre-mixed solution having a concentration by using a monomer acrylamide, a cross-linking agent methylenebisacrylamide, and deionized water. Add a dispersant oleic acid to enable titanium-cobalt powder to suspend in the pre-mixed solution to prepare slurry. Adjust the pH value to 9.0 to 10.0. Next, add a suitable amount of a catalyst N-tetramethylethylenediamine and an initiator ammonium persulfat and stir the mixture even. After air removal, inject the mixture in a mould. The monomer inside the mould undergoes a polymerization reaction to form a mesh-form structure to envelope the titanium-cobalt powder, thereby forming a billet shaped by a macromolecule mesh. The billet undergoes drying, gel exclusion, and sintering to be made into a product. In addition, the porosity and mechanical performance of porous titanium-cobalt alloy may also be changed by adjusting solid content.

In the prior art, for example, a composite interbody vertebral implant for facilitating fusion of adjacent vertebrae is disclosed in U.S. Pat. No. 8,361,150 entitled Composite implant. An upper layer of a porous metal structure and a lower layer of a porous metal structure are included, and a layer of polymeric structure is positioned between the upper layer and the lower layer. The upper layer of a porous metal structure and the lower layer of a porous metal structure allow attachment and in-growth of bone cells. The middle layer of polymeric structure has an effect of adhering the upper layer of a porous metal structure and the lower layer of a porous metal structure and an effect of supporting an entire implant. The overall composite implant has the effect of achieving fusion of an upper vertebra and a lower vertebra. Such a technology is expensive; also, the upper and lower layers have a single-porosity porous structure, resulting in low stability.

SUMMARY OF THE INVENTION

An objective of the present invention is to provide an intervertebral implant, which is formed of a plurality of metal balls having a uniform particle diameter, and has a number of areas, each area having a different porosity and pore size based on a different forming quantity of metal balls, thereby providing an intervertebral implant of a composite pore structure having multiple stiffness, and each area having an even pore distribution and generating an even stress, so that the intervertebral implant achieves a better effect to bear a stress.

The present invention mixes a pore-making agent and a plurality of metal powder particles having a uniform particle diameter, and next obtains an intervertebral implant through sintering. Therefore, a porosity and pore size of the intervertebral implant may be controlled by directly adjusting a weight percentage of the pore-making agent mixed in the metal powder particles, thereby achieve desired mechanical performance. Furthermore, the present invention utilizes a fixture having a bone support forming area and a bone growth forming area, where mixtures having different weight percentages of the pore-making agent mixed in the metal powder particles are filled, respectively, thereby forming an intervertebral implant having a bone support area and a bone growth area, and the bone support area and the bone growth area have different porosities and pore sizes, enabling the intervertebral implant to achieve a multiple stiffness effect without needing any polymeric material.

The intervertebral implant of the present invention is a porous structure formed of a plurality of metal balls, and the intervertebral implant includes a bone support area and a bone growth area. The bone support area and the bone growth area each have a plurality of connecting holes, and a porosity of the bone support area is smaller than that of the bone growth area.

As discussed above, in an embodiment, the porous structure is formed of a plurality of metal balls obtained by performing vacuum sintering on the plurality of metal powder particles mixed with the pore-making agent.

As discussed above, in an embodiment, the plurality of metal balls included in the bone support area and the plurality of metal balls in the bone growth area each have a uniform particle diameter.

As discussed above, in an embodiment, when the plurality of metal powder particles and the pore-making agent are mixed, the pore-making agent has a weight percentage between 1 wt % and 70 wt %.

As discussed above, in an embodiment, the plurality of metal balls has a particle diameter between 10 µm and 100 µm.

As discussed above, in an embodiment, the plurality of connecting holes each has a pore diameter size between 50 µm and 500 µm.

As discussed above, in an embodiment, the bone support area and the bone growth area each have a porosity between 10% and 90%.

As discussed above, in an embodiment, the bone support area and the bone growth area have an elastic modulus between 0.17 GPa and 30 GPa.

As discussed above, in an embodiment, the pores of the porous structure are evenly distributed.

To achieve the foregoing objective, the present invention provides a method of fabricating an intervertebral implant, which includes: providing a fixture, the fixture being divided into a bone support forming area and a bone growth forming area; next, mixing metal powder particles and a pore-making agent to form a first mixture and a second mixture, where the content of the pore-making agent in the first mixture is smaller than that of the pore-making agent in the second mixture; next, filling the first mixture in the bone support forming area, filling the second mixture in the bone growth forming area, and finally performing vacuum sintering to form an intervertebral implant having a bone support area and a bone growth area, where a porosity of the bone support area is smaller than that of the bone growth area.

The intervertebral implant of the present invention is formed of a plurality of metal balls having a uniform particle diameter, and has a number of areas, each area being filled with a mixture having a different weight percentage of the pore-making agent mixed in the metal powder particles. After vacuum sintering, each area has a different quantity of metal balls, and is formed into a porous structure having a different porosity and pore size. The porous structures enable bone growth in pores, thereby improving degree of fusion of the implant and a bone, and pores of each area are evenly distributed and pore sizes are uniform; therefore, generated stress are also uniform, thereby achieving higher mechanical compatibility.

In the intervertebral implant of the present invention, because each layer has a different porosity and pore size, the intervertebral implant can also achieve a multiple stiffness effect without needing a polymeric material, and also when being placed between lumbar vertebras, the intervertebral implant can bear various stresses generated from lumbar movement, so the intervertebral implant has a wide range of bearable stresses and high stability.

The present invention mixes a pore-making agent and a plurality of metal powder particles, and performs sintering to obtain an intervertebral implant. Therefore, a porosity and pore size of the intervertebral implant can be controlled by adjusting a weight percentage of the pore-making agent mixed in the metal powder particles, thereby achieving desired stiffness performance.

The intervertebral implant of the present invention is a bionic-heterogeneous porous titanium alloy medical material that is closer to the mechanical performance of a human intervertebral disc, so that a better effect to bear a stress intervertebrally during body movement is achieved.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
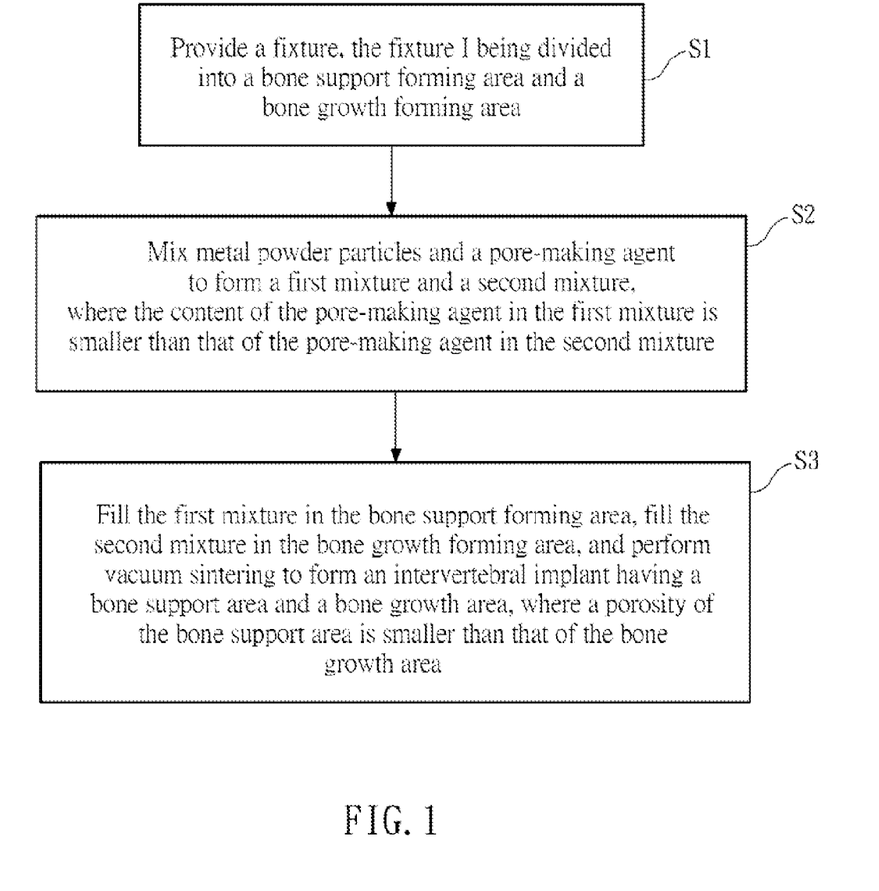
FIG. 1 is a flow chart of a method of fabricating an intervertebral implant according to the present invention.
Figure 2:
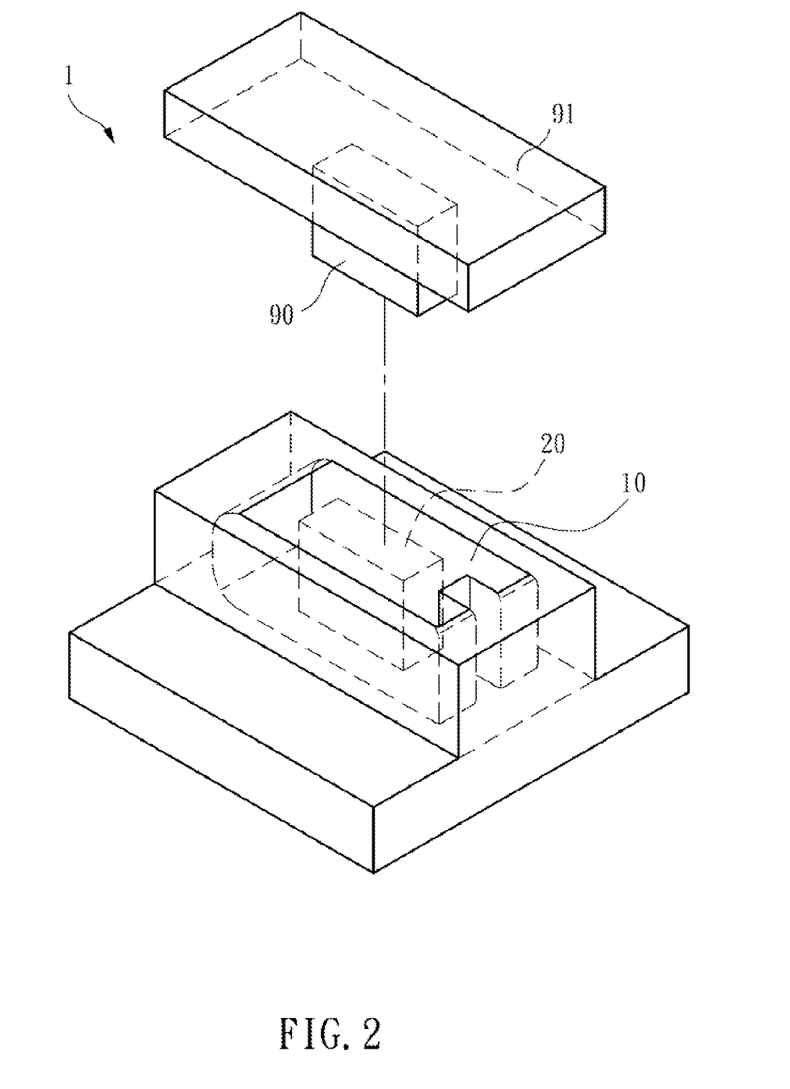
FIG. 2 is a schematic exploded view of a fixture in a method of fabricating an intervertebral implant according to the present invention.

To further understand the objectives, structural features, and functions of the present invention, related embodiments will be illustrated in detail below with reference to the accompanying drawings:

Please refer to FIG. 1 and FIG. 2. FIG. 1 is a flow chart of a method of fabricating an intervertebral implant according to the present invention. FIG. 2 is a schematic exploded view of a fixture in a method of fabricating an intervertebral implant according to the present invention.

A method of fabricating an intervertebral implant of the present invention includes the following steps: First, in Step S1, provide a fixture 1, the fixture 1 being divided into a bone support forming area 10 and a bone growth forming area 20, a central block 90, and a top cover 91.

The fixture 1 is a mould of an intervertebral implant designed according to desired stiffness performance through simulation and drawing by using a computer.

The bone growth forming area 20 of the fixture 1 is the central block 90 that can be freely taken out.

An alkaline liquid is used to clean the surface of the fixture 1. The PH value of the alkaline liquid is greater than 9.

Figure 3A:
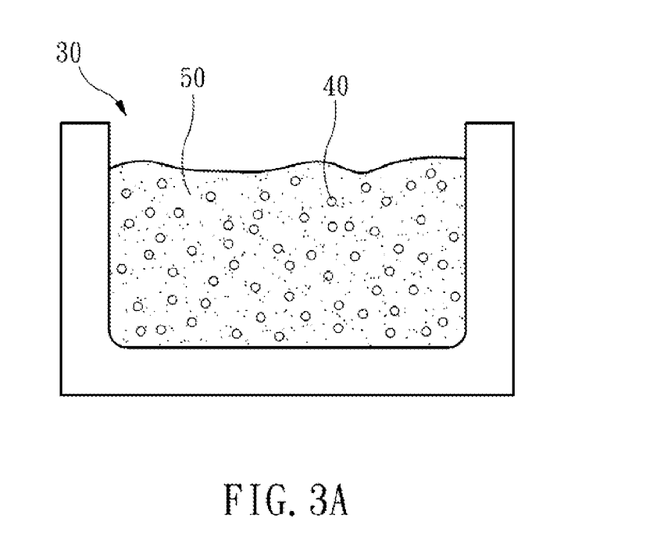
FIG. 3A is a schematic view of a first mixture in a method of fabricating an intervertebral implant according to the present invention.
Figure 3B:
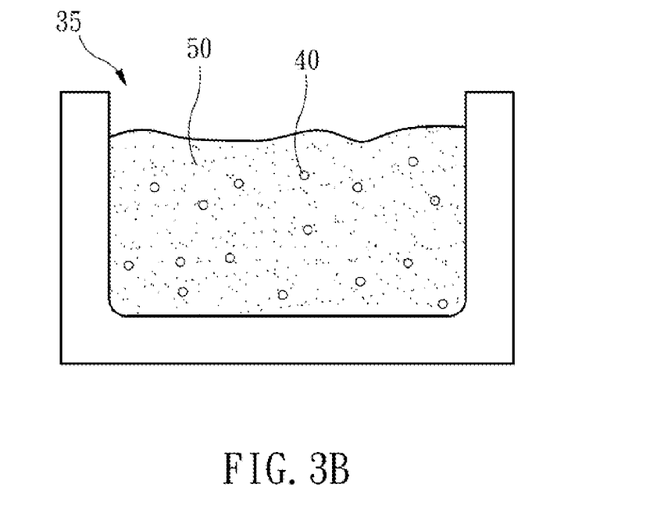
FIG. 3B is a schematic view of a second mixture in a method of fabricating an intervertebral implant according to the present invention.

Next, please refer to FIG. 3A and FIG. 3B. FIG. 3A is a schematic view of a first mixture in a method of fabricating an intervertebral implant according to the present invention. FIG. 3B is a schematic view of a second mixture in a method of fabricating an intervertebral implant according to the present invention. In Step S2, mix metal powder particles 40 and a pore-making agent 50 to form a first mixture 30 and a second mixture 35. The content of the pore-making agent 50 in the first mixture 30 is smaller than that of the pore-making agent 50 in the second mixture 35. That is, the weight percentage of the pore-making agent 50 in the first mixture 30 is smaller than that of the pore-making agent 50 in the second mixture 35.

In the first mixture 30 and the second mixture 35, the metal powder particles 40 are evenly distributed in the pore-making agent 50.

As discussed above, in an embodiment, the metal powder particles 40 in the first mixture 30 and the second mixture 35 have a uniform particle diameter. However, the present invention is not limited thereto, and as designed according to desired stiffness, the metal powder particles 40 in the first mixture 30 and the second mixture 35 have different particle diameters.

As discussed above, in an embodiment, the metal powder particles are titanium or titanium alloy, and the particle diameters are between 10 μm and 100 μm.

As discussed above, in an embodiment, the pore-making agent 50 is in the form of powder, highly thick slurry or plastic solid, so that the first mixture 30 and the second mixture 35 are compressed and shaped.

Figure 4A:
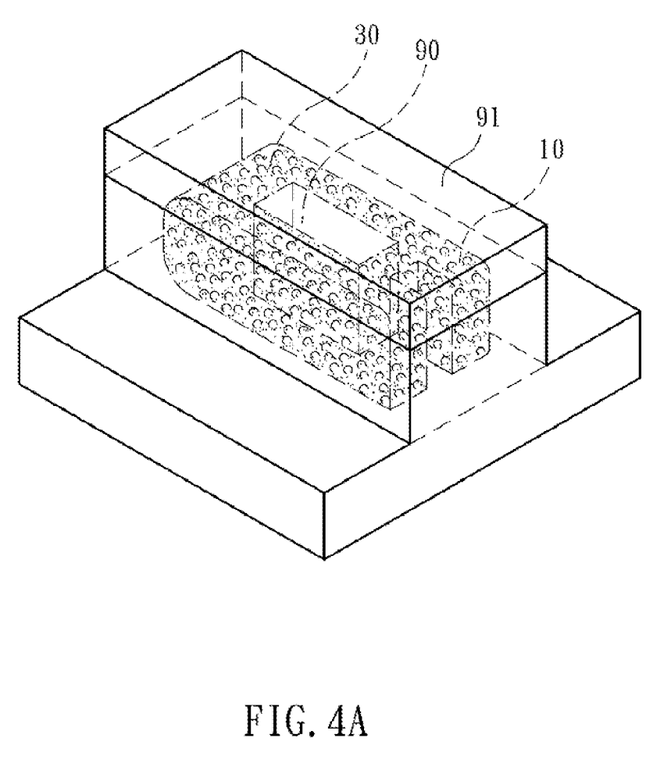
FIG. 4A to FIG. 4C are schematic views of the fixture being filled with a first mixture and a second mixture in a method of fabricating an intervertebral implant according to the present invention.
Figure 4B:
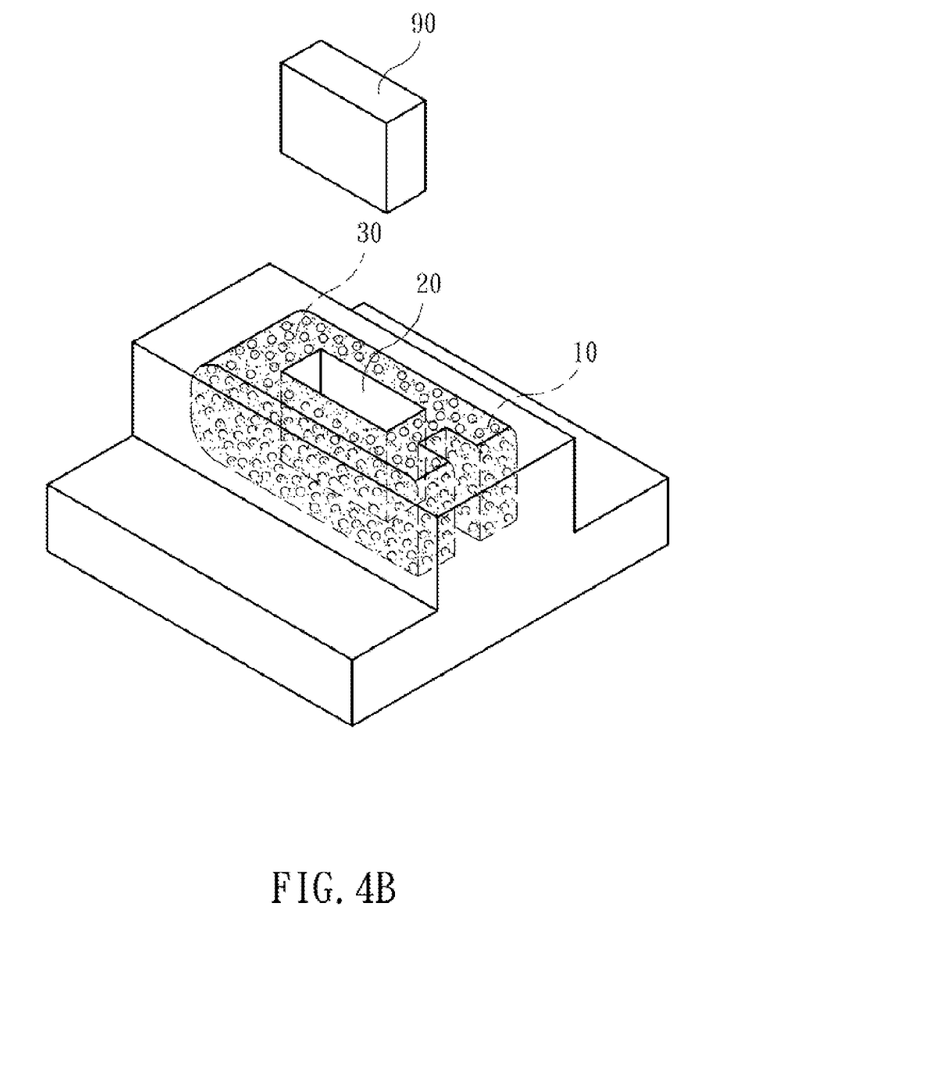
Figure 4C:
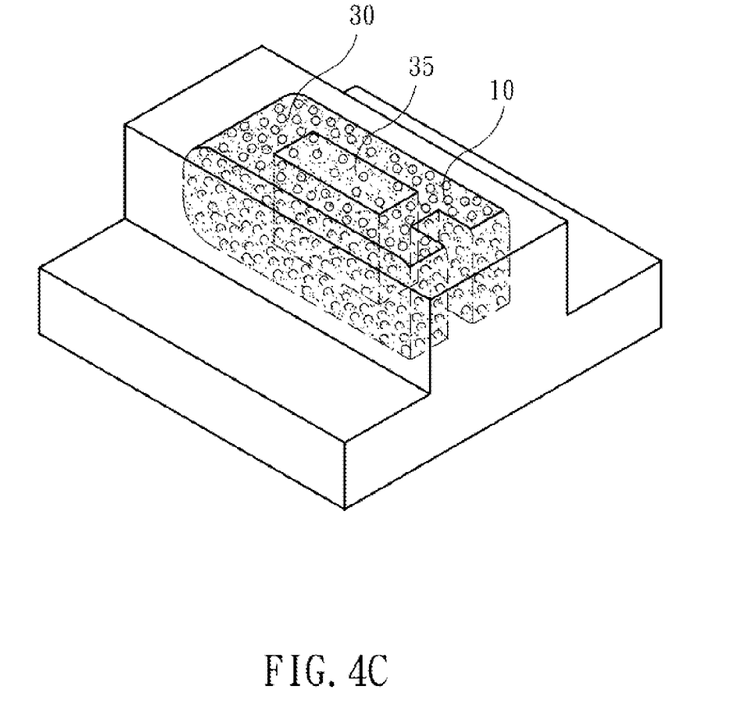
Figure 5:
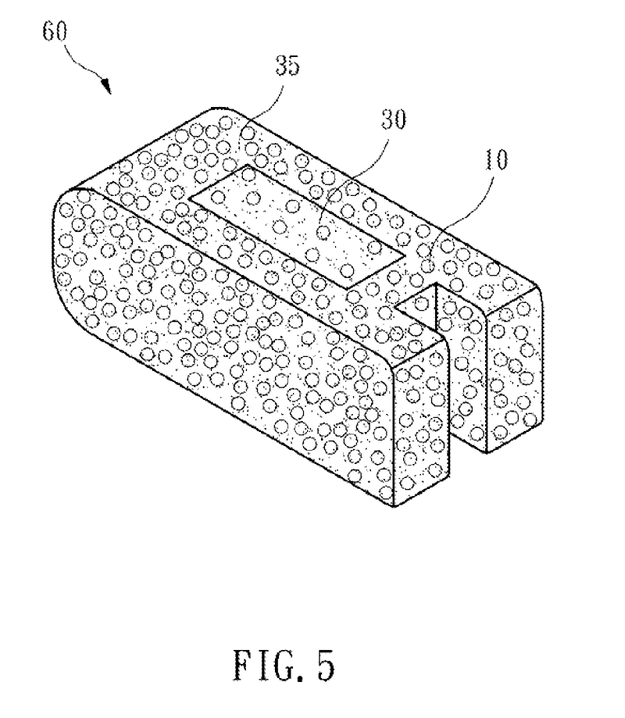
FIG. 5 is a schematic view of a metal billet in a method of fabricating an intervertebral implant according to the present invention.

Next, please refer to FIG. 4A to FIG. 4C and FIG. 5. FIG. 4A to FIG. 4C are schematic views of a fixture being filled with a first mixture and a second mixture in a method of fabricating an intervertebral implant according to the present invention. FIG. 5 is a schematic view of a metal billet of a method of fabricating an intervertebral implant according to the present invention. In Step S3, fill the first mixture 30 in the bone support forming area 10, fill the second mixture 35 in the bone growth forming area 20, and perform compression using the top cover 91 and the central block 90 to form a first metal billet having a shape corresponding to the bone support forming area 10, as shown in FIG. 4A.

Next, open the top cover 91 to take out the central block 90. Here, the bone growth forming area 20 is a cavity, and the cavity has a shape corresponding to the central block 90, as shown in FIG. 4B.

Next, fill the second mixture 35 in the bone growth forming area 20, as shown in FIG. 4C, and perform compression by using the top cover 91 to form a second metal billet 60, as shown in FIG. 5.

Figure 6:
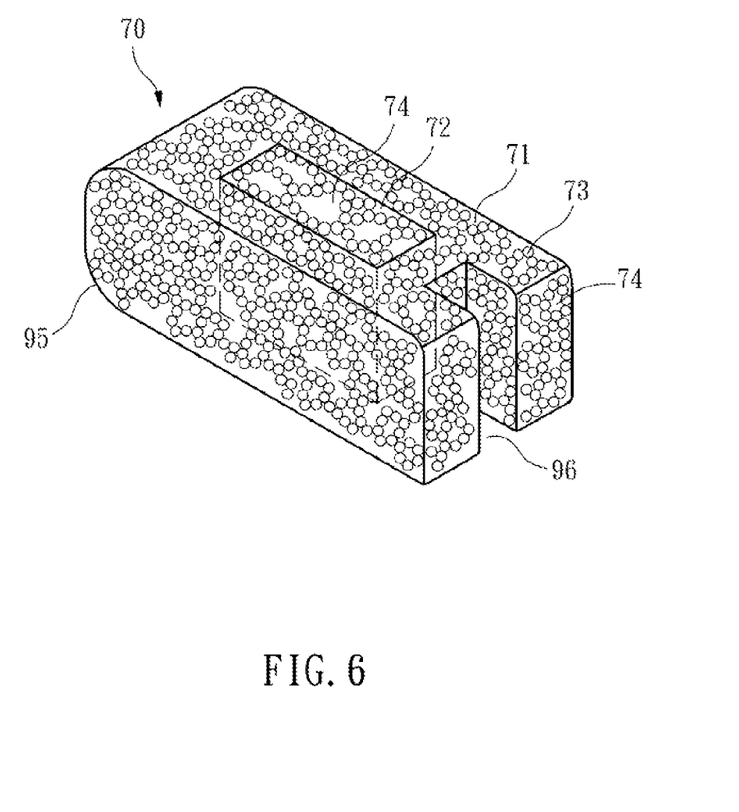
FIG. 6 is a perspective view of an intervertebral implant according to the present invention.

Please refer to FIG. 6. FIG. 6 is a perspective view of an intervertebral implant according to the present invention. For clear presentation of FIG. 6, the outer shape of the intervertebral implant is represented by solid lines, and the shape of a bone growth area 72 is represented by dotted lines.

Next, perform vacuum sintering on the second metal billet 60. After vacuum sintering, an intervertebral implant 70 having a bone support area 71 and the bone growth area 72 is formed, and a porosity of the bone support area 71 is smaller than that of the bone growth area 72.

The present invention forms an intervertebral implant 70 based on the foregoing fabrication method. The intervertebral implant 70 is a porous structure formed of a plurality of metal balls 73, and the intervertebral implant 70 includes the bone support area 71 and the bone growth area 72. The bone support area 71 and the bone growth area 72 each have a plurality of connecting holes 74. As discussed in Step S2 above, because the content of the pore-making agent 50 in the first mixture 30 is smaller than that of the pore-making agent 50 in the second mixture 35, after sintering of the second metal billet 60, the porosity of the bone support area 71 is smaller than that of the bone growth area 72.

As discussed above, in an embodiment, the porous structure is formed of the plurality of metal balls 73 obtained by performing vacuum sintering on the plurality of metal powder particles 40 mixed with the pore-making agent 50. Therefore, the metal balls 73 and the metal powder particles 40 have approximately the same particle diameter, and the particle diameters of the metal ball 73 are between 10 μm and 100 μm.

As discussed in Step S2 above, because the metal powder particles 40 in the first mixture 30 and the second mixture 35 have a uniform particle diameter, the plurality of metal balls included in the bone support area 71 and the bone growth area 72 have a uniform particle diameter.

As discussed in Step S2 above, when the plurality of metal powder particles 40 and the pore-making agent 50 are mixed, the weight percentage of the pore-making agent 50 is between 1 wt % and 70 wt %, and the pore-making agent 50 is mainly ammonium bicarbonate or polymethylmethacrylate (PMMA). However, the present invention is not limited thereto, and the pore-making agent 50 may further be a polymeric material.

As discussed above, in an embodiment, the plurality of connecting holes 74 each has a pore diameter size between 50 μm and 500 μm. The bone support area 71 and the bone growth area 72 each have a porosity between 10% and 90%. The bone support area 71 and the bone growth area 72 have an elastic modulus between 0.17 GPa and 30 GPa.

As discussed in Step S2 above, because the metal powder particles 40 in the first mixture 30 and the second mixture 35 are evenly distributed in the pore-making agent 50, after sintering, pores formed in the porous structure of the intervertebral implant 70 are evenly distributed.

The intervertebral implant of the present invention 70 further includes a design of an arc surface 95, making it easy to place the intervertebral implant between vertebrae during a procedure. In addition, the intervertebral implant 70 further includes an instrument holding portion 96 to facilitate jig holding, so as to improve the efficiency of surgical work.

As discussed above, the intervertebral implant 70 includes structures of a bone support area 71 and a bone growth area 72, which have different porosities and pore sizes. However, the present invention is not limited thereto, the intervertebral implant may be designed with a fixture into structure having a number of areas, and then mixtures containing different weight percentages of the pore-making agent are further prepared. The innermost layer is filled with the mixture containing the highest weight percentage of the pore-making agent; sequentially, a subsequent layer outer side the innermost layer is filled with a mixture containing a lower weight percentage of the pore-making agent. Next, perform vacuum sintering to form an intervertebral implant having a number of areas, so that the intervertebral implant has multiple stiffness.

The intervertebral implant of the present invention is formed of a plurality of metal balls having a uniform particle diameter, and has a number of areas, each area being formed with a different quantity of uniform metal balls because of a different weight percentage of the pore-making agent added in the metal powder particle and each area therefore having a different porosity and pore size, making the intervertebral implant a composite pore structure having multiple stiffness. Because the intervertebral implant has multiple stiffness, when the intervertebral implant is placed between lumbar vertebrae, the intervertebral implant can bear various stresses generated from lumbar movement.

Also, the pores in each layer of the intervertebral implant are evenly distributed, which improves the efficiency of fusion of a growing bone and the lumbar vertebra implant.

The intervertebral implant having a composite pore structure of the present invention is a bionic-heterogeneous porous metal implant medical material that is closer to the mechanical performance of a human intervertebral disc, so that when a lumbar vertebra implant is placed between human vertebrae, a better effect to bear a stress intervertebrally during body movement is achieved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An intervertebral implant, being a porous structure formed of a first plurality of metal balls and a second plurality of metal balls, comprising:
   a bone support area; and
   a bone growth area;
   wherein the bone support area and the bone growth area each have a plurality of connecting holes, and a porosity of the bone support area is smaller than that of the bone growth area;
   wherein the bone support area and the bone growth area have an elastic modulus between 0.17 GPa and 30 GPa;
   wherein the bone support area is comprised of the first plurality of metal balls and each metal ball of the first plurality of metal balls has a first particle diameter, and the bone growth area is comprised of the second plurality of metal balls and each metal ball of the second plurality of metal balls has a second particle diameter; and
   wherein the first particle diameter is different from the second particle diameter.

2. The intervertebral implant according to claim 1, wherein the porous structure is formed of the first plurality of metal balls and the second plurality of metal balls obtained by performing vacuum sintering on a plurality of metal powder particles mixed with a pore-making agent.

3. The intervertebral implant according to claim 2, wherein when the plurality of metal powder particles and the pore-making agent are mixed, a weight percentage of the pore-making agent is between 1 wt % and 70 wt %.

4. The intervertebral implant according to claim 1, wherein the first plurality of metal balls and the second plurality of metal balls have a particle diameter between 10 μm and 100 μm.

5. The intervertebral implant according to claim 1, wherein the plurality of connecting holes each has a pore diameter size between 50 μm and 500 μm.

6. The intervertebral implant according to claim 1, wherein the bone support area and the bone growth area each have a porosity between 10% and 90%.

7. The intervertebral implant according to claim 1, wherein pores of the porous structure are evenly distributed.

* * * * *